United States Patent [19]

Schoonover et al.

[11] 4,329,149
[45] May 11, 1982

[54] METHOD FOR SPECTROPHOTOMETRIC COMPENSATION FOR COLORIMETRIC REAGENT VARIATION

[75] Inventors: David J. Schoonover, Loveland; Paul Larson, Fort Collins, both of Colo.

[73] Assignee: Hach Chemical Company, Loveland, Colo.

[21] Appl. No.: 127,724

[22] Filed: Mar. 6, 1980

[51] Int. Cl.³ .................... G01N 21/27; G01N 21/78
[52] U.S. Cl. .................... 23/230 R; 356/36; 356/407; 356/408
[58] Field of Search ............ 23/230 R; 356/36, 407, 356/408

[56] References Cited

U.S. PATENT DOCUMENTS

| | | | |
|---|---|---|---|
| 3,874,794 | 4/1975 | Schmitt | 356/36 |
| 3,953,136 | 4/1976 | Hach | 23/230 R X |
| 3,954,336 | 5/1976 | Baird | 356/36 |
| 3,976,428 | 8/1976 | Link | 23/230 R |
| 4,003,706 | 1/1977 | Szekely | 23/230 R |
| 4,095,272 | 6/1978 | Janzen | 23/230 R X |
| 4,102,646 | 7/1978 | Sleeter | 23/230 R |
| 4,250,159 | 2/1981 | Cowley | 23/230 R X |
| 4,270,925 | 6/1981 | Isa | 23/230 R |

OTHER PUBLICATIONS

J. A. Howell et al., Microchemical Journal, 15, 598-606, (1970).

*Primary Examiner*—Sidney Marantz
*Attorney, Agent, or Firm*—Leydig, Voit, Osann, Mayer & Holt, Ltd.

[57] ABSTRACT

A method for compensating for error in amount of indicator added to a sample under test in bleaching chemistry analysis involves adding a reagent system comprising an indicator and a dye in relative amounts such that the indicator at one wavelength (the "measuring" wavelength) and the dye at a different wavelength (the "reference" wavelength) exhibit the same absorbance at zero concentration of the parameter of interest. Error in the amount of indicator added to the sample is compensated for by measuring the decrease in absorbance at the measuring wavelength after reaction of the indicator with the parameter of interest, against the absorbance at the reference wavelength.

6 Claims, No Drawings

METHOD FOR SPECTROPHOTOMETRIC COMPENSATION FOR COLORIMETRIC REAGENT VARIATION

RELATED APPLICATIONS

Hach, Andersen and Clemens application Ser. No. 127,725 filed on even date herewith for: "Fluid Analyzer".

BACKGROUND OF THE INVENTION

1. Field of the Invention

The present invention relates generally to spectrophotometry, and, more particularly, concerns a method of compensating for error in the amount of indicator added to a sample in bleaching chemistry analyses.

2. Description of the Prior Art

Chemical analyzers such as, for example, spectrophotometers, automatic chemical analyzers and the like, for monitoring a wide variety of water parameters have long been known to the art and industry. Typically, such analyzers read a color change produced by the addition to the sample of a suitable reagent to indicate the concentration of the substance for which the test is designed. Color changes are efficiently detected by sensing transmitted light filtered to the particular color, or wavelength, involved in the given test. By well known analytical methods, the parameter concentration may be ascertained. Single beam and double beam analyzers are the apparatus commonly used for carrying out such methods.

Chemical analyzers have been thus very effective and successful where "conventional" chemistries have been used in a given test. In such tests, the presence and concentration of a parameter of interest are indicated by an increase in absorbance at the selected wavelength. The indicator is typically added to the sample in an amount in excess of the amount needed to react with all parameter expected to be found in the sample so that the amount of parameter in the sample can be accurately ascertained. Neither the parameter of interest nor the indicator, individually, contribute to the absorbance read by the instrument at the wavelength which is being measured. The sample parameter readily combines with the indicator reagent to form a color (i.e., absorbance change) which is measured by the instrument. Since the indicator is added in excess, any color change in the sample is attributed only to the sample parameter. By known methods, the parameter concentration may then be determined. Obviously, the exact amount of indicator added to the sample is not critical to the analysis. More particularly, when conventional chemistries are used in conjunction with chemical analyzers to conduct the desired test, error in the amount of indicator added to, that is, metered into, successive samples does not affect the accuracy of the analysis so long as the indicator is added in excess.

On the other hand, in "bleaching" chemistries, i.e., those in which the presence and concentration of a parameter of interest is indicated by a decrease in absorbance at the wavelength being measured, the quantity of indicator added to the sample is critical to the analysis. In this type of analysis an indicator having a strong color, that is, strong absorbance, which the instrument measures at the measuring wavelength, is added to the sample. The indicator combines with the parameter to form a colorless compound at the measuring wavelength. As a result, the color being measured by the instrument is reduced. By known analytical methods, the color change may be used to determine the amount of parameter in the sample.

Obviously, since color reduction is used to determine the amount of parameter present in the sample, regardless of whether the analysis is done with a chemical analyzer, or manually, for accurate and precise analyses it is critical that the exact amount of indicator added to the sample be known. Any error in the amount of indicator added to the sample will cause error in the color measured so that such indicator error will cause an erroneous analytical result. Thus, for example, if the amount of indicator in one analysis is lower than in another analysis, the color measured will be reduced in the former analysis in comparison to the latter one. As a result, it will appear that more bleaching has occurred in the former analysis, thus erroneously signalling an increase in the parameter concentration.

This problem is troublesome whenever bleaching chemistry analysis is used to monitor parameter concentration, and is particularly troublesome when automatic chemical analyzers are used to monitor, for example, process water effluent where successive water samples are continuously analyzed for the purpose of determining the parameter concentration. Any variation in the amount of reagent metered into (added to) successive samples will result in erroneous color change measurements from sample to sample thereby adversely effecting the accuracy and precision of the monitoring function. Moreover, neither single wavelength analyzers nor double beam analyzers can compensate for indicator variations in bleaching chemistry analyses, and particularly chemical analyzers, so as to eliminate the error caused by such variations.

One technique commonly used to compensate for sample turbidity and color uses single beam dual wavelength optics to conduct the given test. A beam of light is split so that a portion of the light is directed through a filter to a reference detector and another portion of the light is directed through a filter to a sample detector. The wavelength of the sample and reference filters are chosen on the basis of the parameter being tested and the likely interferences to be found in the sample, respectively. Thus, the light passing through the filter to the reference detector is attenuated by sample turbidity or color and the light passing through the filter to the sample detector is attenuated by the color produced by the reaction of parameter with indicator. Accordingly, the reference detector produces a reference signal related to sample turbidity or color, to which the signal from the sample detector can be compared. Signals from the two detectors are fed to an electrical system which finds the logarithm of the ratio between the sample and reference signals to produce a parameter reading for the sampled water.

SUMMARY OF THE INVENTION

To compensate for indicator variations where bleaching chemistry analysis is used for a given test, the method of the present invention adds to the water sample being tested to reagent system comprising an indicator and a dye in relative amounts such that the indicator at one wavelength (the "measuring wavelengths") and the dye at a different wavelength (the "reference wavelength") exhibit the same absorbance at zero concentration of the parameter of interest. In this fashion, if the amount of the reagent system metered into the water sample is less than the amount desired, the absorbance of the dye at the reference wavelength will be lowered to the same extent as that of the indicator at the measuring wavelength. The potential error resulting from the indicator "short fall" is eliminated by measuring the decreased absorbance at the measuring wavelength (after reaction of the indicator with the parameter of interest) against the absorbance at the reference wavelength.

It is the primary aim of the present invention to provide a method for compensating for error in amount of indicator added to a sample in bleaching chemistry analyses.

Another object of the invention is to provide a method for compensating for error in amount of indicator added to a sample in automatic chemical analyzers. A related object is to provide such a method so that expensive metering and sample/indicator proportioning systems need not be utilized for bleaching chemistry automatic analyzer applications.

Yet another object is to provide a method for compensating for sample flow and sample/indicator mixing variations.

These and other objects and advantages of the invention will become apparent upon reading the following detailed description of the invention.

While the invention will be described in connection with a preferred embodiment, it will be understood that we do not intend to limit the invention to that embodiment. On the contrary, we intend to cover all alternatives, modifications and equivalents as may be included within the spirit and scope of the invention as defined by the appended claims. As an example, while the present invention will be described herein in relation to the chlorophenol red method for determing chlorine dioxide, it should be appreciated that the invention is equally applicable to any other bleaching chemistry analysis.

DETAILED DESCRIPTION OF THE PREFERRED EMBODIMENT

In general, the present invention is predicated on the discovery that reagent system, comprising an indicator and a dye in relative amounts such that the indicator at one wavelength (the measuring wavelength) and the dye at a different wavelength (the reference wavelength) exhibit the same absorbance at zero concentration of the parameter of interest, may be added to a water sample under test to compensate for variations or error in the amount of indicator added to the sample to detect the parameter of interest. The method of the present invention is useful where bleaching chemistry analyses, such as, for example, the chlorophenol red method for chlorine dioxide, are used for the given test. It is particularly useful, where bleaching chemistries are used with chemical analyzers such as, for example, those described in U.S. Pat. No. 3,953,136 and the Hach, Andersen and Clemens, previously identified and filed on even date herewith.

The indicator provides a color at the measuring wavelength which is, of course, indicative of the amount of indicator in solution. When parameter is present in the sample, the color provided by the indicator is bleached by the parameter so that an increase in parameter concentration will be read by the instrument as a decrease in absorbance at the measuring wavelength. Thus, the decrease in absorbance is indicative of the amount of parameter in the sample. The measuring wavelength may be selected on the basis of a plot of absorbance versus wavelength to determine the wavelength of greatest absorbance for a given concentration of indicator. Thus, in the chlorophenol red method for chlorine dioxide, absorbance or chlorophenol red is maximized at 570 nm. Accordingly, that wavelength is preferred.

The dye may comprise any material which absorbs radiant energy at a reference wavelength which is different from the measuring wavelength. The dye is present in the reagent system in an amount relative to the indicator such that absorbance of the dye at the reference wavelength is equal to absorbance of the indicator at the measuring wavelength, at zero concentration parameter. Thus, in terms of absorbance, the amount of indicator and amount of dye in the reagent system are the same. Moreover, absorbance of the dye at the reference wavelength varies only with the amount of reagent system metered into the sample under test. In other words, the dye is not bleached by the parameter of interest so that absorbance of the dye at the reference wavelength is not affected by the presence of parameter.

In addition to the absorbance characteristics described above, dyes suitable for use should be soluble in water, compatible with the indicator and with the parameter so as not to interfere with the indicator/parameter reaction and should not react with the indicator. However, the dye may combine directly with the parameter in a "conventional" fashion, that is, exhibit an increase in absorbance with an increase in parameter concentration, as that would merely increase the sensitivity of the analysis.

The reference wavelength for a given analysis may be determined from a plot of absorbance versus wavelengths for various concentrations of dye to determine the wavelength and concentration of dye needed to meet the above criteria.

The preferred dye for the chlorine dioxide method is picric acid, and the preferred reference wavelength is 410 nm.

The reagent system is composed to contain both the indicator and the dye in the relative amounts heretofore described so as to achieve the desired absorbance characteristics for the system. Thus the indicator and dye are added to the sample under test together in a mixture.

In accordance with the method of the present invention, a reagent system of the type described above is added to the water sample under test. The parameter of interest in the sample bleaches the indicator, causing, at the measuring wavelength, a decrease in absorbance, which is measured against the absorbance at the reference wavelength. Since the absorbance of the dye and absorbance of the indicator are equal at zero parameter of interest, the difference in absorbance so found is the change in absorbance due to the parameter of interest.

By measuring the decrease in absorbance at the measuring wavelength (caused by the reaction of the indicator with the parameter of interest) against the absorbance at the reference wavelength, the potential error in the amount of reagent system added to the sample as, for example, a metering inaccuracy in one or more of successive water samples from an effluent stream, is eliminated. More particularly, and as an example, when ten percent less of the reagent system is added than is desired, the absorbance at the measuring wavelength will obviously be reduced. However, since the dye is added together with the indicator, the absorbance at the reference wavelength will likewise be reduced to the same extent. As a result, for a given sample, the absorbance of the dye and of the indicator will always be at the same level relative to one another regardless of the actual amount of reagent system added to that sample.

It will be appreciated that while the invention has been described in terms of absorbance that it is not so limited. In certain chemical analyzers, such as, for example, analyzers of the single beam, dual wavelengths type described in U.S. Pat. No. 3,953,136 and the copending Hach, Andersen and Clemons previously identified herein, the different in the logarithm of the output signals at a reference sensing detector and at a measuring sensing detector (at the wavelength of absorbance for the dye and wavelength of absorbance of the indicator, respectively,) may be found. That difference, which is indicative of the change in absorbance due to the presence of the parameter of interest, is utilized to compensate for errors in the amount of indicator added to the sample.

It should be noted that depending on the parameter, indicator and dye, it may be necessary to adjust the pH of the sample to optimize the analysis. In the chlorine dioxide analysis, for example, it is preferred to adjust the sample pH from about 5.1 to about 5.5 so that the reaction of chlorine dioxide with chlorophenol red is complete. Accordingly, a buffer which does not add color to the system is first added to the sample to adjust the pH to the desired range. The preferred buffer is a citric acid-sodium citrate buffer.

Furthermore, it may be desirable to adjust the pH after the indicator-parameter reaction has taken place to intensify the color so as to increase the sensitivity of the absorbance measurement at the measuring wavelength. In the chlorine dioxide analysis it is preferred to adjust the sample pH to about 11. Accordingly, a buffer which does not add color is added to the sample after the indicator has reacted with the parameter of interest to raise the pH at about 11, at which pH the absorbance of the indicator at 570 nm and the absorbance of the dye at 410 nm are determined. The difference between the absorbances at these wavelengths is then found. The difference is used to determine the amount of parameter of interest by well known methods.

While the invention has been described in connection with the analysis of chlorine dioxide by the chlorophenol red method, it should be apparent that the invention is equally applicable to other water and waste water analysis, such as, for example, the analysis of fluoride by the Spadns method, the analysis of chlorine by the methyl orange method and chemical oxygen demand (COD), where bleaching chemistries are used in the analysis.

It should be appreciated that while the reagent system has been described as comprising an indicator and a dye, it is within the contemplation of the present invention that the reagent system may comprise merely an indicator for the parameter under test which absorbs radiant energy at a first (measuring) wavelength, which is a function of parameter concentration, and at a second (reference) wavelength which is a function of indicator concentration, such that, the absorbance at the measuring and reference wavelengths are equal at zero sample parameter concentration. An indicator of that nature provides a reference against which the relative color change in the indicator, due to the presence of the parameter of interest, can be measured.

EXAMPLE

This Example illustrates the absorptive characteristics of the reagent system utilized in connection with the chlorophenol red method for chlorine dioxide.

Tests on three separate water samples containing, respectively 0.0 mg/l $ClO_2$, 0.5 mg/l, $ClO_2$ and 1.0 mg/l $ClO_2$ were conducted. Initially, each of the samples was buffered to a pH of about 5.3 with a sodium citrate-citric acid buffer. To the buffered solution was added the reagent system comprising 0.2 mg/l Eastman No. 2116 chlorophenol red, 0.82 mg/l picric acid, and 0.18 mg/l NaOH. The final reagent, 0.178 1/1 2-amino-2-methyl-1-propanol is added to the sample to adjust the pH of the sample of about 11. At this pH, the almost colorless solution is changed to red for easier measurement.

The absorbance of the solution was found at 570 nm and 410 nm using the apparatus described in copending Hach, Andersen and Clemens, previously described herein. It was found with increasing $ClO_2$ concentration that the absorbance at 570 nm decreased linearly and that the absorbance at 410 nm remained substantially constant, the slight changes being of no practical significance. Thus, it is apparent that the present invention can be utilized to eliminate error in the amount of indicator added to a sample under test in the chlorophenol red method for $ClO_2$.

We claim:

1. A method for spectrophotometrically compensating for error in the amount of indicator added to a sample in bleaching chemistry analyses comprising,
   (a) adding to said sample a reagent system comprising an indicator whose absorbance at a first wavelength is a function of the amount of a parameter of interest in said sample and a dye whose absorbance at a second wavelength is equal to the absorbance of said indicator at said first wavelength at zero concentration parameter so that the dye provides a reference against which any change in absorbance may be measured;
   (b) measuring the absorbance at said first and second wavelengths;
   (c) finding the difference of the absorbance at said first wavelength from the absorbance at said second wavelength; and
   (d) relating said difference of absorbances to the amount of the parameter of interest in said sample.

2. The method of claim 1 wherein the indicator is chlorophenol red and the dye is picric acid.

3. A method for spectrophotometrically compensating for mixing and metering variations in bleaching chemistry analyses in a single beam dual wavelength chemical analyzer, comprising, in successive samples under test,
   (a) adding to said sample a reagent system capable of absorbing radiant energy at two wavelengths, the absorbance at a first wavelength being a function of an amount of a parameter in said sample and the absorbance at a second wavelength being a function of said reagent system added to said sample to conduct the tests, said absorbances at said first and second wavelengths being equal at zero parameter concentration;
   (b) detecting the radiant energy at said wavelengths with a sensing means that has an output signal indicative of the radiant energy detected;

(c) finding the difference of the logarithm of said sensing means signal at the first wavelength from the logarithm of the sensing means signal at said second wavelength; and
(d) relating said difference of logarithms to the amount of the parameter of interest.

4. The method of claim 3 wherein the reagent system comprises an indicator and a dye.
5. The method of claim 3 wherein the reagent system comprises an indicator.
6. The method of claim 4 wherein the indicator is chlorophenol red and the dye is picric acid.

* * * * *

UNITED STATES PATENT AND TRADEMARK OFFICE
CERTIFICATE OF CORRECTION

PATENT NO. : 4,329,149
DATED : May 11, 1982
INVENTOR(S) : Schoonover et al.

It is certified that error appears in the above—identified patent and that said Letters Patent is hereby corrected as shown below:

Column 4, line 60, after "sample" insert --such--.

Column 5, line 11, delete "different" and substitute --difference--

Signed and Sealed this

Thirteenth Day of July 1982

[SEAL]

Attest:

Attesting Officer

GERALD J. MOSSINGHOFF
*Commissioner of Patents and Trademarks*